United States Patent
Bayer et al.

(10) Patent No.: US 10,272,183 B2
(45) Date of Patent: Apr. 30, 2019

(54) IMPLANT AND METHOD FOR MANUFACTURING SAME

(75) Inventors: Ullrich Bayer, Admannshagen-Bargeshagen (DE); Wolfgang Schultz, Rostock (DE); Nils Venohr, Kritzmow (DE); Johannes Riedmueller, Nuremberg (DE); Martina Schroeder, Koesterbeck (DE)

(73) Assignee: BIOTRONIK AG, Buelach (CH)

( * ) Notice: Subject to any disclaimer, the term of this patent is extended or adjusted under 35 U.S.C. 154(b) by 849 days.

(21) Appl. No.: 13/164,127

(22) Filed: Jun. 20, 2011

(65) Prior Publication Data

US 2011/0319982 A1  Dec. 29, 2011

Related U.S. Application Data

(60) Provisional application No. 61/358,425, filed on Jun. 25, 2010.

(51) Int. Cl.
*A61F 2/82* (2013.01)
*A61L 31/02* (2006.01)
*A61L 31/08* (2006.01)
*A61L 31/14* (2006.01)
*A61L 31/18* (2006.01)

(52) U.S. Cl.
CPC ........... *A61L 31/022* (2013.01); *A61L 31/088* (2013.01); *A61L 31/148* (2013.01); *A61L 31/18* (2013.01); *Y10T 156/10* (2015.01); *Y10T 156/1052* (2015.01); *Y10T 156/1062* (2015.01)

(58) Field of Classification Search
CPC ..................................... A61F 2/82; A61F 2/06

USPC ....................................................... 623/1.34
See application file for complete search history.

(56) References Cited

U.S. PATENT DOCUMENTS

2004/0143317 A1* 7/2004 Stinson ................. A61L 31/022
                                                           623/1.15
2004/0193255 A1* 9/2004 Shanley .................... A61F 2/91
                                                           623/1.42

(Continued)

FOREIGN PATENT DOCUMENTS

EP       2184038 A2   5/2010
EP       2198899 A2   6/2010
WO    2004089247 A1  10/2004

OTHER PUBLICATIONS

EP11168167 European Search Report dated Jul. 24, 2014.

*Primary Examiner* — Matthew Schall
(74) *Attorney, Agent, or Firm* — Wagenknecht IP Law Group, PC

(57) ABSTRACT

The present invention relates to an implant, in particular an intraluminal endoprothesis, comprising a body containing a metallic material, and comprising at least one functional element that is fastened to the body and has a material composition in at least a portion of its volume that differs from the material of the body, the material composition preferably including radio-opaque and/or x-ray opaque material. To effectively prevent accelerated degradation due to the formation of a local cell of the material of the body and the functional element, the at least one functional element includes a first layer at least in the region of its surface where it is bonded to the body, the first layer primarily containing at least one metal oxide. Furthermore, the manufacture of an implant of this type is described.

13 Claims, 2 Drawing Sheets

(56) References Cited

U.S. PATENT DOCUMENTS

2005/0283226 A1* 12/2005 Haverkost .................... 623/1.15
2010/0161030 A1* 6/2010 Bayer ................... A61L 31/022
                                                              623/1.15

\* cited by examiner

IMPLANT AND METHOD FOR MANUFACTURING SAME

CROSS REFERENCE TO RELATED APPLICATIONS

This invention claims benefit of priority to U.S. patent application Ser. No. 61/358,425 filed on Jun. 25, 2010; the contents of which are herein incorporated by reference in their entirety.

TECHNICAL FIELD

The present invention relates to an implant, in particular an intraluminal endoprothesis, comprising a body that is at least partially composed of a metallic material, and comprising a functional element and to a method for manufacturing such an implant.

BACKGROUND

Stents are endovascular prostheses (endoprotheses) or implants that can be used to treat stenoses (vasoconstrictions). They usually comprise a body in the form of a hollow-cylindrical or tubular matrix lattice that is open at both longitudinal ends of the tubes. The tubular matrix lattice of an endoprosthesis of this type is inserted into the vessel to be treated, and is used to support the vessel. Further fundamental body shapes are also possible. Furthermore, the present invention relates to implants that can be used in the field of orthopedic surgery e.g. for the skull region, and, in particular, to implants that have low x-ray visibility due to their small size and wall thickness.

The invention can also be used for stents in neurovascular applications. In that case, absorbable Mg stents are used to hold open the blood vessels that supply the brain. These systems are used in the field of preventing acute ischemic strokes.

Stents or other implants often contain metallic materials in their body. The metallic materials can form a biodegradable material, although they can also contain polymeric, biodegradable materials.

"Biodegradation" is understood to mean hydrolytic, enzymatic, and other metabolic degradative process in the living organism, which are caused primarily by the bodily fluids that come in contact with the endoprothesis and result in a general disintegration of at least large portions of the implant. The term "biocorrosion" is often used as a synonym for the term "biodegradation". The term "bioresorption" includes the subsequent resorption of the degradative products by the living organism. The objective of using biodegradable implants is for them to be broken down by the organism at a point in time when they are no longer needed e.g. for their supporting effect, and therefore do not remain in the organism as a foreign object for any longer than necessary.

Materials (basic material) that are suitable for the body of biodegradable implants can be composed of one material or a plurality of materials. Examples of suitable polymeric compounds are polymers of the group cellulose, collagen, albumin, casein, polysaccharide (PSAC), polylactic acid (PLA), poly-L-lactide (PLLA), polyglycol (PGA), poly(D, L-lactide-co-glycolide) (PDLLA-PGA), polyhydroxybutyric acid (PHB), polyhydroxy valeric acid (PHV), poly (alkyl carbonate), poly(orthoester), polyethylenterephtalat (PET), polymalonic acid (PML), polyanhydride, polyphosphazene, polyamino acids and their copolymers, and hyaluronic acid. Depending on the properties that are desired, the polymers can be present in pure form, in derivatized form, in the form of blends, or as copolymers. Metallic biodegradable materials are based on alloys of magnesium, iron, zinc, and/or tungsten.

The present invention relates to implants having a body, the material of which contains a metallic material. Further metallic materials in addition to the above-mentioned biodegradable materials are feasible for use. In particular, the present invention relates to implants having the component magnesium, which preferably forms the main component of the body material.

The position of a stent or other implants is often determined using imaging methods e.g. using an x-ray device. Due to the small atomic number and the low density of the biodegradable material magnesium and its alloys, the x-ray visibility of the medical implants made of these materials is very low. To eliminate this disadvantage, it is known to provide medical devices with functional elements that have a material composition in at least a portion of their volume that differs from the material of the body. The so-called "(x-ray) markers" or functional elements contain a material, in particular, that absorbs x-rays and/or other electromagnetic rays to a greater extent (referred to below as x-ray opaque or radio-opaque material) than the material of which the body is composed.

Publication DE 10 2006 038 238 A1 describes an x-ray marker for medical implants made of a biocorrodible metallic material, and a medical implant having an x-ray marker of this type, wherein the x-ray marker is a boride or carbide of the elements tantalum or tungsten. A marker thusly composed has low x-ray absorption, however, since the mean atomic number and the density of these materials are low.

Publication US 2009/0204203 A1 discloses an implant in the form of a bioabsorbable stent having one or more radio-opaque markers. A receiving device (marker support) on the body of the stent, in which the marker is fastened, is passivated or oxidized before the marker is applied. This slows the corrosion of the receiving device, thereby resulting in improved endothelialization.

Furthermore, publication DE 10 2008 054 845 A1 proposes a mechanical anchoring of tantalum- or tungsten markers to magnesium stents, followed by plasma-chemical treatment of this bond. The method described therein has the disadvantage, however, that the mechanical anchoring of markers e.g. by riveting or laser- or electron-beam welding is technologically highly complex and requires extreme fine-motor skills and/or complex and therefore expensive handling techniques. Furthermore, after the passivation layer has degraded, the metallic contact of tantalum or tungsten to magnesium, even if the latter has been initially passivated from the outside, results in accelerated degradation since the materials of the x-ray marker form a local cell with the body material.

As described above, in the case of implants having a body composed of a metallic material, the problem arises with the disposition of metallic functional elements on the body that contact corrosion can occur in the contact region between the material of the body and the material of the functional element. This results in accelerated degradation, or in the separation of the functional element from the body, and therefore the implant is either no longer capable of performing its function, or it cannot be found. The above-described devices from the prior art contain no solutions, or inadequate solutions, to the problem described herein.

SUMMARY

A feature of the present invention, therefore, is to create an implant with which increased degradation in the region of the functional element is prevented and, simultaneously, high bond strength is realized. The object is furthermore to provide a cost-effective method for manufacturing an implant of this type.

A feature described above is solved by an implant, in the case of which the at least one functional element includes a first layer at least in the region of its surface where it is bonded to the body, the first layer primarily containing at least one metal oxide.

Such an implant, according to the invention, has the advantage that metallic contact between the material of the functional element and the material of the body is prevented from the start by the first layer which contains at least one metal oxide and is fixedly disposed on the surface of the functional element. As a result, the formation of a local cell between the body and the functional element can be prevented, even in an advanced stage of degradation, in which the degradation has reached the boundary surface between the functional element and the body. The first layer, which contains a metal oxide, also has the advantage that its porosity makes it easier to connect the functional element to the body. As explained below in greater detail, a further advantage of the solution according to the invention is that the first layer is created, preferably using a thermal treatment or an electrically induced annealing treatment, before the functional element is fastened to the body. Thus, the surroundings of the functional element on the implant body do not need to be thermally stressed, which is an advantage in particular due to the low melting point or melting range of the magnesium alloys (approximately 600° C. to 650° C.) that are preferably used. In a heat treatment, the functional element is stored for a certain period of time in an oven or another heatable space having a specified temperature. In electrically induced annealing treatment, the functional element is connected in an electrical circuit and is annealed for a defined period of time due to the current, which flows at a specified direct voltage, and due to the internal resistance.

As an alternative, the first layer can be created using a plasma-chemical treatment of the functional element, preferably using a CORR treatment. In the CORR treatment, higher final voltages (preferably greater than 400 V) and higher current densities (preferably greater than 25 mA/cm$^2$) are used than in conventional plasma-chemical treatment.

In a preferred embodiment, the body contains at least one largely biodegradable metallic material, preferably magnesium or a magnesium alloy, as the main component. These materials degrade within a period of time that is desirable for many applications.

In a development of the invention, the at least one functional element contains a metal or a metal alloy that includes at least one metal from the group having the elements tungsten, tantalum, and titanium, and, in its first layer, contains at least one oxide of the group having the compounds tungsten oxides, tantalum oxides, and titanium oxides. The stated materials of the functional element have good x-ray absorption properties and are very easily provided, via surface oxidation, with an oxide layer (first layer) that is impermeable, passivating, and insulating (i.e. electrically non-conductive), even when the layer thicknesses are small. Thus they allow a functional element to be designed with a minimal size.

Even better x-ray visibility is attained when the at least one functional element has a jacket comprising a metal or a metal alloy that includes at least one metal from the group having the elements tungsten, tantalum, and titanium, and a core that preferably contains a metal or a metal alloy that includes at least one metal of the group having the elements platinum and gold.

The jacket of the functional element need not enclose the core entirely. It is merely necessary for the jacket to enclose the core at least in the region in which the functional element is fastened to the body. It is thereby ensured that the materials platinum and gold, and their alloys, do not come in contact with the material of the body and thereby form a local cell which, in the case of gold or platinum, would cause even greater degradation of the body.

In a further preferred embodiment, the thickness of the first layer is 1 µm to 20 µm, preferably 1 µm to 10 µm. Due to the stated thickness of the first layer, which contains metal oxide, it is ensured that the functional element is adequately electrically insulated from the body.

In a further preferred embodiment, the at least one functional element is fastened to the body using an adhesive, preferably a polymer-based adhesive. To be precise, it was recognized that a simple connection that does not mechanically stress the filigree body is attained using a bonded connection in particular. In addition, a form-fit connection can be realized by adapting the shape of the functional element and the shape of the recess (opening) in the body of the implement, into which the functional element is inserted.

It was recognized that conventional technologies for fastening x-ray markers to a body, such as riveting, crimping, laser- and electron-beam welding, cannot be used easily for the materials magnesium or magnesium alloys. Compared to other materials used for implants, such as Nitinol, magnesium or magnesium alloys have a lower elastic modulus and a lower yield point which, if the functional element were fastened, would result in excessive thermal and/or mechanical stressing of the body in the region in which the functional element is disposed, and thereby result in early, undesired plastic deformation.

Polyurethane or a degradable polymer (e.g. PLLA L210, PLLA L214) can be used as an advantageous polymer-based adhesive. These adhesives are particularly biocompatible and provide good electrical insulation.

The object described above is furthermore solved by a method for manufacturing an implant of this type, which has the following step:

Fasten at least one functional element to the body, which has a material composition in at least a portion of its volume that differs from the material of the body, the material composition preferably including radio-opaque and/or x-ray opaque material, wherein the at least one functional element includes a first layer, via which it is connected to the body and which primarily contains at least one metal oxide.

The method according to the invention is a cost-effective method for manufacturing an implant having the advantages described above.

As explained above, it is advantageous when the at least one functional element is fastened to the body by bonding, preferably using a polymer-based adhesive.

In a particularly preferred embodiment, the functional element is cut from a wire- or bar-shaped semi-finished product, wherein the semi-finished product preferably contains a metal or metal alloy that includes at least one metal from the group having the elements tungsten, tantalum, and titanium, or preferably has a jacket comprising a metal or a metal alloy that includes at least one metal from the group having the elements tungsten, tantalum, and titanium, and a core that preferably contains a metal or a metal alloy that includes at least one metal of the group having the elements platinum and gold.

A wire- or bar-shaped semi-finished product of this type can preferably have a diameter of 200 µm to 400 µm.

As an alternative, the functional elements to be fastened to the implant can also be made available as circular blanks or pellets having a circular, oval, or polygonal cross section They are preferably provided with the first layer before they are placed on the body. They can be fastened to the body of the implant e.g. by bonding them in a corresponding opening or recess.

After the first layer has been created on the surface of the semi-finished product using a thermal treatment, individual functional elements can be obtained very cost-effectively from a wire- or bar-shaped semi-finished product by cutting off individual sections of the semi-finished product. They can then be placed in a receiving device, which has been formed on the body and which includes e.g. a cylindrical recess or opening, and glued therein. To this end, the corresponding receiving device (also referred to as an eyelet, below) is manufactured with an oversize of approximately 20 µm. Before the functional element is glued in the eyelet, the functional element is immersed in a polymer solution, and the functional element is subsequently situated in the eyelet. The functional element may be fastened in the eyelet before or after it is cut from the semi-finished product. The adhesive is then cross linked and, therefore, cured e.g. using a thermal treatment such a treatment using IR radiation.

The wire- or bar-shaped semi-finished product can have a cross section that is e.g. circular, oval, or polygonal (e.g. triangular, square, or pentagonal). It is advantageous when the recess or opening in the eyelet, which may also be continuous, has a cross-sectional shape that is matched to the cross-sectional shape of the semi-finished product or the functional element, in order to realize an additional form-fit connection.

It is particularly preferable for the wire- or bar-shaped semi-finished product to be provided with at least one predetermined breaking point preferably before it is fastened to the body, and/or preferably before the first layer is created. This predetermined breaking point makes it possible to separate individual functional elements from the semi-finished product using a minimum amount of force. The diameter of the predetermined breaking point preferably does not exceed approximately 30% of the diameter of the semi-finished product. The predetermined breaking point is preferably created using a material-removing method e.g. turning.

In a further embodiment, the predetermined breaking point, which was initially formed in the semi-finished product preferably mechanically e.g. using a separating or cutting tool, is deepened further using a process step that is carried out before the functional element is fastened to the body, and which is carried out to form the first layer, e.g., a thermal treatment, an electrically induced annealing treatment, or a plasma-chemical treatment of the semi-finished product, the predetermined breaking point being reduced e.g. to a residual cross section of the semi-finished product at the predetermined breaking point of 20 µm to 70 µm. As a result, only a small amount of force is required to detach (e.g. using nippers) the section of the semi-finished product, which should actually form the functional element, from the remainder of the semi-finished product.

The thermal treatment for curing the adhesive may be carried out before or after the functional element is separated from the semi-finished product.

A further advantage is obtained when the functional element is fastened to the body after a laser-beam cutting of the body has been performed. The rough laser-cut edge increases the adhesion of the glue or the other fastening agent to the body.

Subsequent thereto, one or more further process steps may be carried out to create the final shape of the implant, such as manual deburring, reaming, and finishing the inner and outer surfaces using abrasive mandrels (inner) and/or sleeves (outer). This process also removes overhanging sections or edges of the functional element.

The implant can then be subjected to electropolishing and/or a plasma-chemical treatment. The further process steps that proceed the electropolishing and/or plasma-chemical treatment, and that were mentioned in the previous paragraph, can also be eliminated.

In terms of the plasma-chemical treatment and/or electropolishing, a further advantage of the implant according to the invention is that the functional element is decoupled from the body by the first layer, and therefore the plasma-chemical method and/or the electropolishing produces a layer containing oxides and possibly phosphates only on the surface of the body, and which can be adjusted in terms of its composition and thickness in accordance with the desired duration of degradation.

In the plasma-chemical treatment (coating), a pulsed voltage is applied to the body, the amplitude of which exceeds, over a portion of the treatment period, a bath voltage that is characteristic for the material of the body, and that preferably increases over the course of the treatment.

In a preferred embodiment, the current density in the plasma-chemical treatment is at least approximately 4 mA/cm$^2$.

Anodic contacting of the body is used for the plasma-chemical treatment. The contacting material is an aluminium or titanium wire. The implant is then immersed in an aqueous solution that preferably contains phosphates. After application of a pulsed, continually increasing bath voltage that is characterized by long pulse pauses, the body material oxidizes. The plasma-chemical effects result in the production of a mixed phase of oxides and, possibly, phosphates of the body material. It is advantageous when the respective oxide layers grow slowly since the oxide having the highest enthalpy of formation otherwise cannot form a coherent layer. According to the invention, the slow growth of the oxide layer is attained by using long pauses between the voltage pulses. They can be up to 500 milliseconds long.

The plasma-chemical treatment creates a structure on the metal of the body which is porous due to the method used, and which makes it easier to subsequently seal the component, e.g. with a polymeric cover layer, due to improved adhesion, or which can be used as a carrier or a substrate (e.g. for a pharmaceutically active substance or other functional substances).

A "pharmaceutically active substance" (or therapeutically active or effective substance) is understood to mean a plant-based, animal-based, or synthetic active agent (drug) or a hormone that is used in suitable doses as a therapeutic agent to influence states or functions of the body, as a replacement for active agents that are produced naturally by human or animal bodies, such as insulin, and to eliminate or render harmless pathogens, tumors, cancer cells, or foreign substances.

After the plasma-chemical treatment, the body is preferably rinsed in a solvent, preferably using distilled $H_2O$, and is then dried preferably at a temperature of at least 80° C., and particularly preferably of at least approximately 100° C., wherein the drying is preferably carried out in a forced-air oven.

A further advantage is obtained when the aqueous solution contains a buffer, preferably potassium dihydrogenphosphate and/or sodium dihydrogenphosphate. As an alternative, or in addition thereto, the aqueous solution can also contain calcium dihydrogenphosphate as the buffer, the low water solubility of which can be increased by adding complexing agents such as ethylene diamine. As a result, phosphates, in particular, are created in the plasma-chemically generated layer on the body.

As a further, final surface treatment in a further embodiment, the implant can be provided with a second layer which contains a degradable polymer, preferably after the plasma-chemical treatment or the electropolishing, and preferably via spraying. The plasma-chemical treatment or electropolishing can also be eliminated. A second layer of this type has a layer thickness of approximately 1 μm to approximately 10 μm, preferably approximately 1 μm to approximately 5 μm. PPLA L210 can be used as the degradable polymer, for example.

The invention is explained in the following in greater detail with reference to embodiments that are depicted in figures. All of the features described and/or depicted graphically form the subject matter of the invention, even independently of their combination in the claims or their back-references.

DETAILED DESCRIPTION

Figure 1:
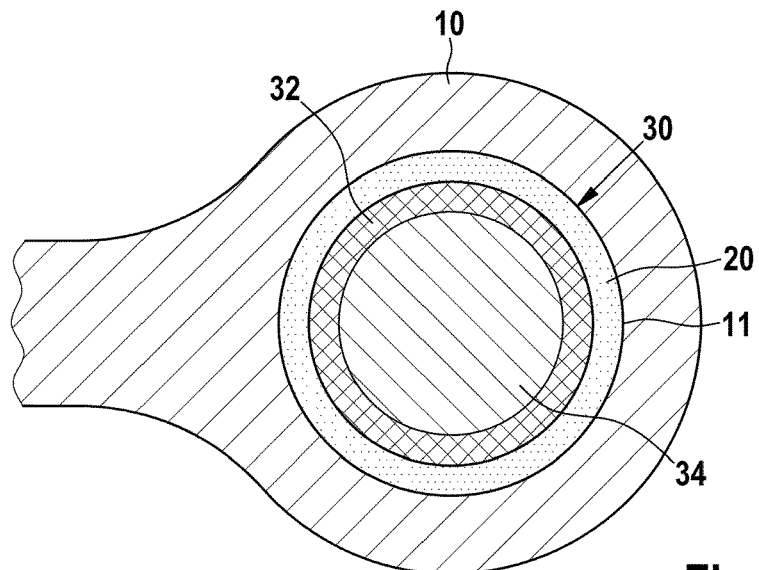
FIG. 1 depicts a cross section of a functional element, which is fastened to a body, of a first embodiment of an implant according to the invention.

FIG. 1 shows a section of a body of an implant, according to the invention, in the form of a medical stent composed of the magnesium alloy WE43 that includes a functional element 30. The illustration shows an eyelet 10 that is disposed e.g. on the distal or proximal end of the body. Preferably, three such eyelets that are offset by 120° are formed as components of the body on the hollow-cylindrical lattice, e.g. on a strut, at the distal and/or proximal end of the body of the implant.

An x-ray opaque functional element 30 that is fastened to eyelet 10 by an adhesive layer 20 is disposed in a cylindrical, continuous recess 11 in eyelet 10, which also forms the inner surface of eyelet 10. Functional element 30 includes a first layer 32, which is composed primarily of tungsten oxides, on its outer surface at which functional element (x-ray marker) 30 is connected to the inner surface of eyelet 10. Functional element 30, which is substantially cylindrical, is composed of tungsten in an inner region 34 underneath or inside first layer 32. First layer 32 is preferably hollow-cylindrical in shape and encloses inner, substantially cylindrical region 34 only on its jacket surface.

Figure 2:
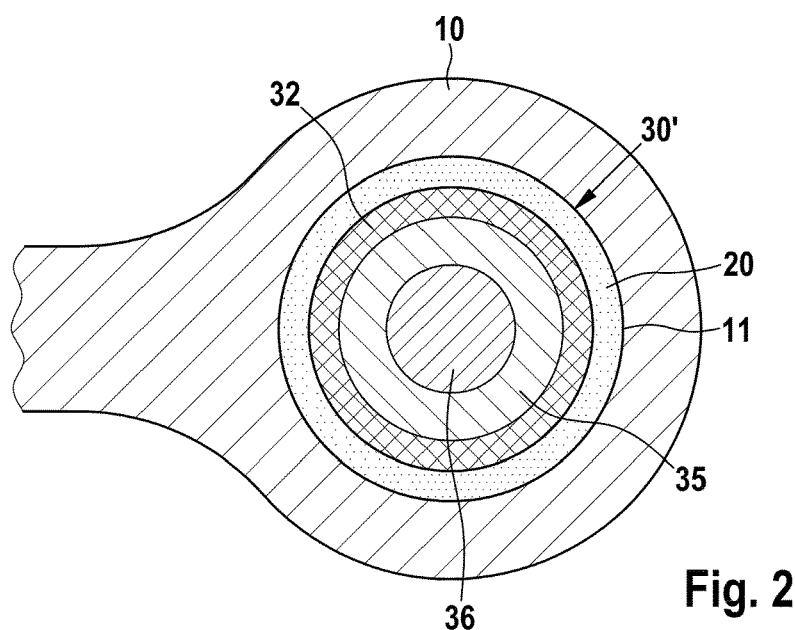
FIG. 2 depicts a cross section of a functional element, which is fastened to a body, of a second embodiment of an implant according to the invention.

In the embodiment shown in FIG. 2, functional element 30' includes, underneath first layer 32 composed primarily of tungsten oxides, a substantially hollow-cylindrical tungsten layer 35 that encloses, in the form of a jacket, a substantially cylindrical core 36 of functional element 30', which is composed e.g. of gold and/or platinum or an alloy of these elements. In this embodiment as well, first layer 32 is preferably hollow-cylindrical in shape and encloses hollow-cylindrical tungsten layer 35 only in the region of its jacket surface. Functional element 30' is even more visible in an x-ray picture due to the higher x-ray density of core 36 compared to the material of inner region 34 of functional element 30 of the first embodiment.

A functional element 30' of this type can have an outer diameter of e.g. 400 μm and a first layer 32 that is approximately 5 μm thick. Tungsten jacket 35, which can be composed of titanium as an alternative, has an outer diameter of 390 μm, for example. The outer diameter of cylindrical core 36 composed of gold and/or platinum or an alloy of these elements can be e.g. 350 μm.

Figure 4:
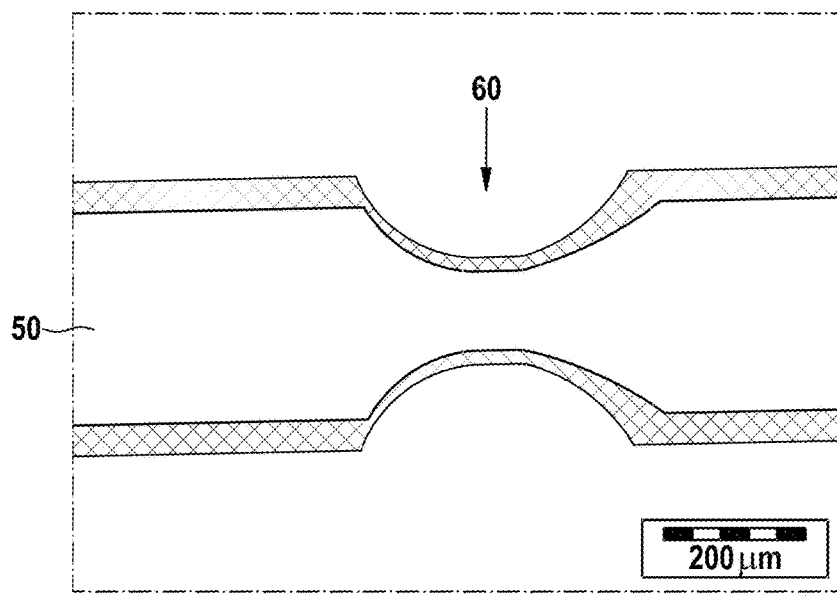
FIG. 4 depicts a tungsten rob having a predetermined breaking point, in a view from the side.

Functional element 30 of the first embodiment, which is shown in FIG. 1, is manufactured, in a first embodiment of the method according to the invention, from a wire-shaped semi-finished product in the form of a bar 50 having a substantially circular cross section (FIG. 4). Bar 50 is composed of tungsten and has a diameter of approximately 400 μm. A bar 50 of this type is provided with predetermined breaking points 60 at intervals of e.g. 120 μm, each predetermined breaking point 60 having a diameter of approximately 30 μm to approximately 80 μm. Predetermined breaking points 60 are created using material-removing methods such as turning (by cutting in using a turning tool or by grinding using a pointed, rapidly rotating abrasive disk having a thickness of e.g. approximately 20 μm). Every section of bar 50 that is separated from a further section by predetermined breaking points 60 should form a functional element 30 at the conclusion of the manufacturing method. A photograph of a section of such a bar 50 composed of tungsten having a predetermined breaking point 60 is shown in FIG. 4. The light regions in the center of bar 50 and the gray edge regions are reflected glare.

Figure 3:
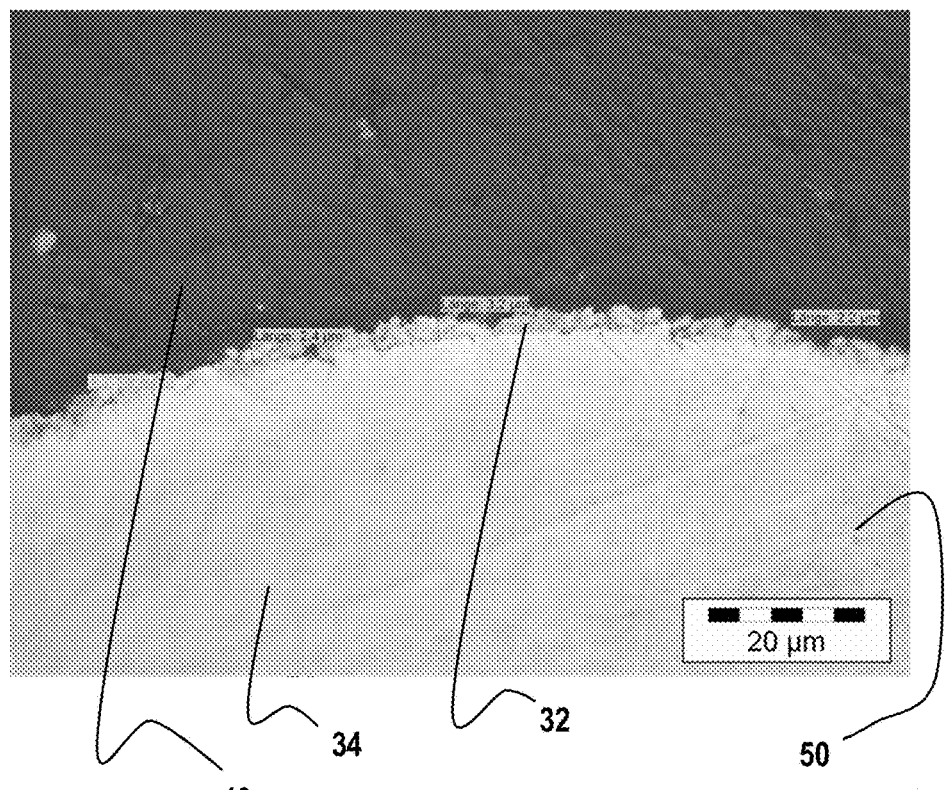
FIG. 3 depicts a transverse section of a tungsten rod having an oxide layer.

A bar 50 of this type which has been provided with predetermined breaking points 60 is now connected to a voltage source. Given a direct voltage of 3 V, an electrical current of 15 A is then applied for a period of 5 seconds. Bar 50 heats up as a result, and heat colors become visible (light yellow in this case). An impermeable oxide layer (first layer 32) having a thickness of approximately 2 μm to 3 μm thereby forms on the surface of bar 50 which is composed primarily of tungsten oxides. A transverse sectional view of a bar 50 which has been thusly treated is shown in FIG. 3. Bar 50 which was provided with first layer 32 was embedded in an embedding medium 40, and a transverse section was created for closer inspection. As shown in the photograph, first layer 32 has a thickness of a few μm. The thicknesses that were measured are between 2.2 μm and 3.2 μm. As an alternative, bars containing tungsten can also be annealed in air in an oven for 2 h at temperatures of approximately 600° C. This results in the formation of oxide layers having a similar thickness.

Due to the above-described passivation of bar 50 via the formation of first layer 32, the metallic residual cross sections of predetermined breaking points 60 are also reduced further, until they have a diameter of approximately 20 μm to approximately 70 μm. The small metallic cross section of predetermined breaking points 60 that now remains has a mechanical strength, bending strength in particular, that suffices for the process of installation into the eyelet. Due to the shearing stress that occurs when nippers are used subsequently to cut, large mechanical forces are not required, however, to break through predetermined breaking points 60.

Bar 50 provided with first layer 32 is then immersed in a polymer of polyurethane (PU), to which a solvent has been added, and, after a dwell time of a few seconds, is removed from the container. The polymer that has adhered to the surface of bar 50 has a layer thickness of approximately 20 μm. The bar is then inserted into opening 11 of eyelet 10 which has an inner diameter of e.g. 450 μm. The stent is fixed onto a mandrel, and exactly that section of the bar that will form the particular functional element is disposed in opening 11 of eyelet 10. The PU adhesive is then cross linked using IR radiation. The PU adhesive hardens as a result, and the section of bar 50 that forms functional element 30 can be separated from the remaining part of bar 50 at predetermined breaking point 60 using nippers. Only a minimal flexural load is produced as a result, thereby ensuring that minimal mechanical stress is applied to the bond between functional element 30 and body (eyelet 10) formed by adhesive 20, and to the filigree body.

Next, the stent including the functional element is deburred, treated using reamers, and/or the inner and outer sides of the stent are ground mechanically, if necessary. Any overhanging regions of functional element 30 are also mechanically removed as a result.

The stent that has been thusly treated is then electropolished in an aqueous solution containing phosphorous. The solution contains, for example:
20 parts by volume of water
30 parts by volume of 85% phosphoric acid
50 parts by volume of ethanol
The bath voltage is approximately 6V (direct voltage).

Functional element 30 is not changed by the electropolishing since it is electrically insulated from the body (eyelet 10) by first layer 32 and adhesive 20.

In a second embodiment, the above-described manufacturing method is carried out using a bar composed of tantalum (instead of tungsten). Deviating from the above-stated parameters for the tungsten bar, in the case of the tantalum bar, a direct voltage of 3V and an electrical current of 10 A are applied for a period of 5 seconds to create first layer 32 (oxide layer containing primarily tantalum oxides).

In a third embodiment of the method according to the invention, a bar that includes a hollow-cylindrical jacket composed of titanium and having an outer diameter of 400 μm and a core composed of gold and having an outer diameter of 350 μm can be used as the semi-finished product for manufacturing the functional element.

In contrast to the first embodiment, the first layer (oxide layer) disposed on the titanium jacket is created using a plasma-chemical treatment (also referred to below as CORR treatment), wherein the first layer contains primarily titanium oxides. The CORR treatment produces a dielectric microporous surface morphology having a thickness of approximately 5 μm, which results in very good cross linking with the adhesive and, therefore, a good bonded connection between the functional element and the body (eyelet). The CORR treatment for the titanium-encased bar is carried out using the same electrolyte composition as used in the plasma-chemical treatment of the body described in the fifth embodiment. The final voltage in the CORR treatment is 480 V, however. The pulse length of the pulsed direct voltage (pulse on) is 5 μs, and the pulse pause (pulse off) is 1000 μs. The current density is approximately 25 mA/cm$^2$. This means that the titanium-encased bar is anodically contacted and immersed in the electrolyte to a freely selectable depth, then a bath voltage is applied that increases from 0V to the final voltage. After a coating time of approximately 2 minutes, the final voltage has been reached, the current supply is interrupted, and the bar is removed from the electrolyte and dried in warm air.

The fourth embodiment corresponds to the second embodiment of the method according to the invention, although a biodegradable polymer e.g. PLLA L210 is used instead of a polyurethane as the adhesive.

The fifth embodiment corresponds to the fourth embodiment of the method according to the invention, although electropolishing is replaced by a plasma-chemical treatment of the body of the implant. To this end, the body is contacted anodically and immersed and oxidized plasma-chemically in an aqueous electrolyte having the following composition (based on 1 liter H$_2$O):
80 g KH$_2$PO$_4$
45 g Na$_2$CO$_3$
65 ml ED (99%)
5 g to 10 g NaOH At bath final voltages of 200 to 500 V and using pulsed currents having an on/off ratio of 5 μs on and 1000 μs off (in the extreme case, up to 5000 microseconds off) and a current density of 1 mA/cm$^2$, a layer forms on the surface of the body that is composed of oxides, mixed oxides, phosphates, and mixed phosphates, and spinels of the particular metallic base material. The bath final voltage to be selected is dependent on the material of the body. For example, a layer thickness of 3 μm is produced on the magnesium alloy surface at a bath final voltage of 260 V. Once this final voltage has been reached, the current density drops to half the value that was originally set. Next, the current supply is terminated, the stent is removed from the bath, rinsed intensively under flowing distilled water, and dried in warm air at approximately 40° C. Finally, the stent is carefully separated from the contacting material, and it is stored dry and in an inert atmosphere until it is processed further.

Subsequently, a second layer of a biodegradable polymer e.g. PLLA L210 or PLLA L214 can be applied by spraying, for example.

The manufacturing method according to the invention can be used to produce implants whose mechanical properties do not change during the fastening of the functional element, or due to the fastening of the functional element. Furthermore, the functional element having the oxide layer is effectively prevented from forming a local cell, which accelerates degradation. The use of an adhesive to connect contact elements and body is advantageous since the porous structure of the oxide layer results in high adhesion by the glue and therefore good adhesion. The contact element is thereby prevented from becoming detached when the implant becomes plastically deformed e.g. when a stent is dilated. In addition, the method according to the invention ensures that the accuracy of the production process is increased and that the system, due to the multilayered design, has a high safety margin against accelerated degradation.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE NUMERALS

10 Eyelet
11 Opening
20 Adhesive layer
30, 30' Functional element
32 First layer
34 Inner region
35 Jacket
36 Core
40 Embedding medium
50 Bar
60 Predetermined breaking point

What is claimed is:

1. An implant in the form of a biodegradable intraluminal endoprosthesis, comprising:
   a biodegradable body that is at least partially composed of a metallic material, and
   a functional element that is fastened to the body, wherein the functional element has a material composition comprising a radio-opaque and/or x-ray opaque metal or metal alloy that differs from the metallic material of the body, fixed directly to the outer surface of the metal or metal alloy of the functional element is a metal oxide to form a first layer outside of the functional element, wherein the first layer prevents contact between the radio-opaque and/or x-ray opaque metal or metal alloy and the body.

2. The implant according to claim 1, characterized in that the body contains at least one biodegradable metallic material comprising magnesium or a magnesium alloy as a main component.

3. The implant according to claim 1, characterized in that the metal or a metal alloy includes at least one metal selected from the group consisting of tungsten, tantalum, and titanium, and the metal oxide is selected from the group consisting of a tungsten oxide, a tantalum oxide, and a titanium oxide.

4. A biodegradable implant in the form of an intraluminal endoprosthesis, comprising:
   a body that is at least partially composed of a metallic material, and
   a functional element that is fastened to the body, characterized in that the functional element comprises a jacket at least partially surrounding a core, wherein the jacket contains at least one metal that is different than the metallic material of the body and is selected from the group consisting of tungsten, tantalum, and titanium, and wherein the core comprises platinum or gold.

5. The implant according to claim 1, characterized in that the thickness of the first layer is approximately 1 mm to approximately 20 mm or approximately 1 mm to approximately 10 mm.

6. The implant according to claim 1, characterized in that the functional element is fastened to the body using an adhesive or a polymer-based adhesive.

7. The implant according to claim 1, wherein the first layer consists of the metal oxide.

8. The implant according to claim 1, wherein the first layer prevents formation of a local cell between the metal or metal alloy and the body.

9. The implant according to claim 1, wherein the first layer electrically isolates the functional element from the body.

10. The implant according to claim 1, wherein the first layer is chemically attached to the functional element and bonded to the body.

11. The implant according to claim 1, wherein the functional element comprises a metal core surrounded by a jacket comprising a metal or metal alloy, wherein the core comprises a higher x-ray density than the jacket.

12. The implant according to claim 4, further comprising a metal oxide layer at least partially covering the jacket to prevent contact between the jacket and the body.

13. An implant in the form of a biodegradable intraluminal endoprosthesis, comprising:
   a biodegradable body that is at least partially composed of a metallic material, and
   a functional element that is fastened to the body, wherein the functional element has a material composition comprising a radio-opaque and/or x-ray opaque metal or metal alloy that differs from the metallic material of the body, fixed directly to the outer surface of the metal or metal alloy of the functional element is a metal oxide to form a first layer outside of the functional element, wherein the first layer prevents contact between the radio-opaque and/or x-ray opaque metal or metal alloy and the body, and wherein the first layer is created by a thermal treatment, an electrically induced annealing treatment or a plasma-chemical treatment of the functional element.

* * * * *